United States Patent
Alghannam et al.

(10) Patent No.: US 11,679,378 B2
(45) Date of Patent: Jun. 20, 2023

(54) METHODS OF PRODUCING ISOMERIZATION CATALYSTS

(71) Applicant: Saudi Arabian Oil Company, Dhahran (SA)

(72) Inventors: Afnan Alghannam, Khobar (SA); Munir D. Khokhar, Dhahran (SA); Sohel K. Shaikh, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 148 days.

(21) Appl. No.: 17/185,257

(22) Filed: Feb. 25, 2021

(65) Prior Publication Data
US 2022/0266230 A1 Aug. 25, 2022

(51) Int. Cl.
| | | |
|---|---|---|
| *B01J 31/02* | (2006.01) | |
| *B01J 21/10* | (2006.01) | |
| *B01J 37/10* | (2006.01) | |
| *C07C 5/25* | (2006.01) | |
| *C07C 11/08* | (2006.01) | |

(52) U.S. Cl.
CPC ........... *B01J 31/0231* (2013.01); *B01J 21/10* (2013.01); *B01J 37/10* (2013.01); *C07C 5/2506* (2013.01); *B01J 2231/52* (2013.01); *C07C 11/08* (2013.01)

(58) Field of Classification Search
CPC ........ B01J 31/0231; B01J 21/10; B01J 37/10; B01J 2231/52; B01J 35/1009; B01J 35/1014; C07C 5/2506; C07C 11/08
USPC .......................................... 502/340; 585/664
See application file for complete search history.

(56) References Cited

U.S. PATENT DOCUMENTS

| | | | |
|---|---|---|---|
| 2,947,708 A | 8/1960 | Wilson et al. | |
| 3,546,313 A | 12/1970 | Banks | |
| 3,586,731 A | 6/1971 | Heckelsberg | |
| 3,702,886 A | 11/1972 | Argauer et al. | |
| 4,024,201 A | 5/1977 | Takahashi | |

(Continued)

FOREIGN PATENT DOCUMENTS

| | | |
|---|---|---|
| CN | 101531558 A | 9/2009 |
| CN | 102325742 A | 1/2012 |

(Continued)

OTHER PUBLICATIONS

U.S. Office Action dated Sep. 13, 2021 pertaining to U.S. Appl. No. 16/701,829, filed Dec. 3, 2019, 31 pages.

(Continued)

*Primary Examiner* — Patricia L. Hailey
(74) *Attorney, Agent, or Firm* — Dinsmore & Shohl LLP

(57) ABSTRACT

Methods of producing an isomerization catalyst include preparing a catalyst precursor solution, hydrothermally treating the catalyst precursor solution to produce a magnesium oxide precipitant, calcining the magnesium oxide precipitant to produce an isomerization catalyst precursor, soaking the isomerization catalyst precursor in an acid solution comprising sulfuric acid to product a isomerization catalyst precursor precipitant, and calcining the isomerization catalyst precursor precipitant to produce the isomerization catalyst. The catalyst precursor solution includes at least a magnesium precursor, a hydrolyzing agent, and cetrimonium bromide. Methods of producing 1-butene from a 2-butene-containing feedstock with the isomerization catalyst are also disclosed.

19 Claims, 4 Drawing Sheets

(56) References Cited

U.S. PATENT DOCUMENTS

| | | | |
|---|---|---|---|
| 4,071,471 A | 1/1978 | Banks et al. | |
| 4,217,244 A | 8/1980 | Montgomery | |
| 4,575,575 A | 3/1986 | Drake et al. | |
| 4,609,769 A | 9/1986 | Kukes et al. | |
| 4,684,760 A | 8/1987 | Drake | |
| 5,026,935 A | 6/1991 | Leyshon et al. | |
| 5,026,936 A | 6/1991 | Leyshon et al. | |
| 5,053,379 A | 10/1991 | Giordano et al. | |
| 5,153,165 A | 10/1992 | Lowery et al. | |
| 6,207,115 B1 | 3/2001 | Chodorge et al. | |
| 6,538,168 B1 | 3/2003 | Schwab et al. | |
| 6,586,649 B1 | 7/2003 | Botha et al. | |
| 6,646,172 B1 | 11/2003 | Schwab et al. | |
| 6,777,582 B2 | 8/2004 | Gartside et al. | |
| 6,875,901 B2 | 4/2005 | Gartside et al. | |
| 6,977,321 B1 | 12/2005 | Dath et al. | |
| 7,214,841 B2 | 5/2007 | Gartside et al. | |
| 7,604,794 B2 | 10/2009 | Tiitta et al. | |
| 7,608,746 B2 | 10/2009 | Setoyama et al. | |
| 7,754,647 B2 | 7/2010 | Schubert et al. | |
| 7,754,934 B2 | 7/2010 | Tsunoda et al. | |
| 7,824,656 B2 * | 11/2010 | Idem | B01J 23/83 502/313 |
| 7,977,522 B2 | 7/2011 | Takai et al. | |
| 8,100,996 B2 | 1/2012 | Simmons et al. | |
| 8,299,313 B2 | 10/2012 | Takai et al. | |
| 8,324,440 B2 | 12/2012 | Popp et al. | |
| 8,343,885 B2 | 1/2013 | Ruettinger et al. | |
| 8,440,874 B2 | 5/2013 | Ramachandran et al. | |
| 8,586,813 B2 | 11/2013 | Ramachandran et al. | |
| 8,722,568 B2 | 5/2014 | Popp et al. | |
| 9,630,167 B2 | 4/2017 | Bordoloi et al. | |
| 9,834,497 B2 | 12/2017 | Shaikh et al. | |
| 9,884,794 B2 | 2/2018 | Al-Khaffaf et al. | |
| 10,005,703 B2 | 6/2018 | Abudawoud et al. | |
| 10,017,873 B1 | 7/2018 | Koo et al. | |
| 10,059,645 B2 | 8/2018 | Shaikh et al. | |
| 10,065,906 B2 | 9/2018 | Shaikh et al. | |
| 10,214,466 B2 | 2/2019 | Shaikh et al. | |
| 10,550,048 B2 | 2/2020 | Alshafei et al. | |
| 2004/0168367 A1 | 9/2004 | Suenaga et al. | |
| 2004/0254411 A1 | 12/2004 | Steinbrenner et al. | |
| 2005/0014981 A1 | 1/2005 | Gartside et al. | |
| 2006/0293548 A1 | 12/2006 | Spamer et al. | |
| 2007/0038010 A1 | 2/2007 | Xie et al. | |
| 2007/0225478 A1 | 9/2007 | Querci et al. | |
| 2010/0041930 A1 | 2/2010 | Gartside et al. | |
| 2010/0234542 A1 | 9/2010 | Blackborow et al. | |
| 2010/0286458 A1 | 11/2010 | Iselborn et al. | |
| 2011/0021858 A1 | 1/2011 | Ramachandran et al. | |
| 2011/0152595 A1 | 6/2011 | Takai et al. | |
| 2011/0196185 A1 | 8/2011 | Krawczyk et al. | |
| 2012/0016172 A1 | 1/2012 | Miyazoe et al. | |
| 2012/0108864 A1 | 5/2012 | Gartside et al. | |
| 2012/0264990 A1 | 10/2012 | Nicholas et al. | |
| 2012/0283090 A1 | 11/2012 | Popp et al. | |
| 2012/0289617 A1 | 11/2012 | Wang et al. | |
| 2013/0058861 A1 | 3/2013 | Idem et al. | |
| 2013/0085311 A1 | 4/2013 | Youn et al. | |
| 2015/0141721 A1 | 5/2015 | Choi et al. | |
| 2016/0237006 A1 | 8/2016 | Stoyanova et al. | |
| 2017/0001925 A1 | 1/2017 | Abudawoud et al. | |
| 2017/0001926 A1 | 1/2017 | Shaikh et al. | |
| 2018/0057425 A1 | 3/2018 | Shaikh et al. | |
| 2018/0104671 A1 | 4/2018 | Sae-Khow et al. | |
| 2018/0208526 A1 | 7/2018 | Alshafei et al. | |
| 2019/0169093 A1 | 6/2019 | Stoyanova et al. | |

FOREIGN PATENT DOCUMENTS

| | | |
|---|---|---|
| CN | 104370676 A | 2/2015 |
| CN | 103772115 B | 8/2015 |
| CN | 108043403 A | 5/2018 |
| CN | 109513457 A | 3/2019 |
| CN | 111111635 A | 5/2020 |
| DE | 10013253 A1 | 9/2001 |
| EP | 0251351 A2 | 7/1988 |
| EP | 304515 B1 | 12/1991 |
| EP | 2236204 A1 | 6/2010 |
| JP | 2006341185 A | 12/2006 |
| WO | 9929805 A1 | 6/1999 |
| WO | 2006089957 A1 | 8/2006 |
| WO | 2009117128 A1 | 9/2009 |
| WO | 2009126769 A2 | 10/2009 |
| WO | 2010019595 A2 | 2/2010 |
| WO | 2011136983 A1 | 11/2011 |
| WO | 2015055594 A1 | 4/2015 |
| WO | 2017003812 A1 | 1/2017 |
| WO | 2017003817 A1 | 1/2017 |
| WO | 2017003821 A1 | 1/2017 |
| WO | 2019001710 A1 | 1/2019 |

OTHER PUBLICATIONS

Duong, T. H. Y. et al., "Synthesis of Magnesium Oxide Nanoplates and Their Application in Nitrogen Dioxide and Sulfur Dioxide Adsorption" Journal of Chemistry, vol. 2019, Article ID 4376429, 9 pages.

Banks et al. "New Developments and Concepts in Enhancing Activities of Heterogeneous Metathesis Catalysts" Journal of Molecular Catalysis, 28, (1985) 117-131, 15 pgs.

Gao et al. "Controlled synthesis of MgO with diverse basic sites and its CO2 capture mechanism under different adsorption conditions" Chemical Engineering Journal 336 (2018) 710-720, 11 pgs.

MOL "Industrial applications of olefin metathesis" Journal of Molecular Catalysis A: Chemical 213 (2004) 39-45, 8 pgs.

Pilarska et al. "Recent development in the synthesis, modification and application of Mg(OH)2 and MgO: A review" Powder Technology 319 (2017) 373-407, 36 pgs.

Zhao et al. "Solvo- or hydrothermal fabrication and excellent carbon dioxide adsorption behaviors of magnesium oxides with multiple morphologies and porous structures" Materials Chemistry and Physics 128 (2011) 348-356, 9 pgs.

Zhao et al. "Mesoporous MgO promoted with NaNO3/NaNO2 for rapid and high-capacity CO2 capture at moderate temperatures" Chemical Engineering Journal 332 (2018) 216-226, 11 pgs.

Examination Report pertaining to GCC Application No. 2016/31672 dated Sep. 13, 2018.

Wu et al., "Investigation on acidity of zeolites bound with silica and alumina", Studies in Surface Science and Catalysis, 143, pp. 217-225, 2002.

Korean Office Action pertaining to Korea Application No. 10-2018-7003238 dated May 14, 2018 (English Translation).

Shaikh et al., "Self-Methathesis of Butenes to Propylene", Catalysis in Petroleum Refining & Petrochemicals, pp. 1-6, Dec. 7-8, 2015.

Debecker et al., "Preparation of Mo03/si02-Al203 methathesis catalysts via wet impregnation with different Mo precursors", Journal of Molecular Catalysis A: Chemical . 340, pp. 65-76, 2011.

Puriwat et al. "Elucidation of the basicity dependence of 1-butene isomerization on MgO/Mg(OH)s catalysts", Catalysis Communications, 2010, pp. 80-85.

Arudra et al., "Silicalite-1 as Efficient Catalyst for Production of Propene from 1-Butene", ACS Catalysis, 2014, 4205-4212, 4, American Chemical Society.

Awayssa et al., "Modified HZSM-5 as FCC Additive for Enhancing Light Olefins Yield from Catalytic Cracking of VGO", Applied Catalysis A: General, 2014, 172-183, 477.

Balcar, et al., "Mesoporous molecular sieves as advanced supports for olefin metathesis catalysts", Coordination Chemistry Reviews 257, 2013, pp. 3107-3124, Czech Republic.

Barrett et al., "The Determination of Pore Volume and Area Distributions in Porous Substances. I. Computations from Nitrogen Isotherms", J. Am. Chem. Soc., 1951 , 373-380, 73(1).

Beck et al., "A New Family of Mesoporous Molecular Sieves Prepared with Liquid Crystal Templates", J. Am. Chem. Soc., 1992, 10834-10843, 114, American Chemical Society.

(56) References Cited

OTHER PUBLICATIONS

Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.

Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.

Bin Hu, et al., "Highly Active Doped Mesoporous KIT-6 Catalysts for Metathesis of 1-Butene and Ethene to Propene: The Influence of Neighboring Environment of W Species", The Journal of Physical Chemistry, ACS Publication, 2013 American Chemical Society, pp. 26385-26395, USA.

Daniell et al., Enhanced Surface Acidity in Mixed Alumina-Silicas: A Low-Temperature FTIR Study:, 2000, 196, 247-260, Elsevier.

Do et al., "Zeolite Nanoclusters Coated onto the Mesopore Walls of SBA-15", J. Am. Chem. Soc., 2004, 14324-14325, 126, American Chemical Society.

International Search Report and Written Opinion dated Nov. 11, 2016 pertaining to International Application No. PCT/US2016/039025.

International Search Report and Written Opinion dated Sep. 14, 2016 pertaining to International Application No. PCT/US2016/039012.

International Search Report and Written Opinion dated Sep. 27, 2016 pertaining to International Application No. PCT/US2016/0038967.

International Search Report and Written Opinion dated Sep. 14, 2016 pertaining to International Application No. PCT/US2016/039013.

Jermy et al., "Utilization of ZSM-5/MCM-41 Composite as FCC Catalyst Additive for Enhancing Propylene Yield from VGO Cracking", J. Porous Mater, 2012, 499-509, 19, Springer.

Kawai et al., "Metaethesis of Halogen-Containing Olefin Over Re2O7/Al2O3 Catalyst Promited with Alkylmetal as a Cocatalyst", Journal of Molecular Catalysis A: Chemical, 1998, 133, 51-59.

Kumar et al., "Performance of Nano Crystalline H-ZSM-5 as Additive in FCC Catalyst: A Review", International Journal of Research in Engineering and Tehnology, May 2014, vol. 3, pp. 481-485.

Lwin et al., "Olefin Metathesis by Supported Metal Oxide Catalysts", ACS Catalysis, 2014, 2505-2520, 4, American Chemical Society.

Office Action pertaining to U.S. Appl. No. 15/190,950 dated Sep. 27, 2017.

Office Action pertaining to U.S. Appl. No. 15/190,964 dated Nov. 2, 2017.

Quignard et al., "Aryloxide Ligands in Metathesis of Olefins and Olefinic Esters: Catalytic Behaviour ofW(OAr)2CIl4 by SnMe4, Sn(n-Bu)4, Pb(n-Bu)4, MgNp2: synthesis of W(OAr)2Cl2(CHCMe3)(OR2) and W(OAr)2Cl(CHCMe3)(CH2CMe3)(OR2)", Journal of Molecular Catalysis, 1986, 36, 13-29.

Ruihua Gao, et al., "High-activity, single-site mesoporous WO3-MCF materials for the catalytic epoxidation of cycloocta-1,5-diene with aqueous hydrogen peroxide", Journal of Catalysis, 256, 2008, pp. 259-267, China.

Wang et al., "Synthesis and Structure of Silicalite-1/SBA-15 Composites Prepared by Carbon Templating and Crystallization", Journal of Materials Chemistry, 2007,4265-4273, 17, The Royal Society of Chemistry 2007.

Wang et al., "Effect of Support Nature on WO3/SiO2 Structure and Butene-1 Metathesis", Applied Catalysis A: General, 2003, 25-37, 250, Elsevier B.V.

Zhao et al., "Effect of Tungsten Oxide Loading on Metathesis Activity of Ethene and 2-Butene Over WO3/SiO2 Catalysts" Transition Met Chem, 2009, 621-27, 34, Springer.

International Preliminary Report on Patentability dated Jan. 11, 2018—PCT/US2016/039012.

International Preliminary Report on Patentability dated Jan. 2, 2018—PCT/US2016/039012.

Non-Final Office Action pertaing to U.S. Appl. No. 15/398,196 dated Jan. 9, 2018.

International Search Report and Written opinion dated Mar. 28, 2018, pertaining to International Application No. 30 PCT/US2018/013945, filed Jan. 17, 2018, 9 pages.

U.S. Office Action dated Apr. 20, 2018 pertaining to U.S. Appl. No. 15/859,794, filed Jan. 2, 2018.

International Search Report and Written Opinion dated Apr. 24, 2018 pertaining to International Application No. PCT/US2018/014131, filed Jan. 18, 2018.

Notice of Allowance dated Apr. 24, 2018 pertaining to U.S. Appl. No. 15/190,964, filed Jun. 23, 2016.

Election/Restriction Requirement dated May 21, 2018, pertaining to U.S. Appl. No. 15/866,772, filed Jan. 10, 2018.

Office Action pertaining to U.S. Appl. No. 15/866,800 dated Jun. 29, 2018.

Office Action pertaining to U.S. Appl. No. 15/190,981 dated Apr. 4, 2017.

Office Action pertaining to U.S. Appl. No. 15/866,772 dated Aug. 28, 2018.

Harmse et al., "On the Product Formation in 1-Butene Methathesis over Supported Tungsten Catalysts", Catal. Lett, vol. 137, pp. 123-131, Apr. 2010.

International Search Report and Written Opinion dated Aug. 7, 2020 pertaining to International application No. PCT/US2020/032805 filed May 14, 2020, 15 pgs.

International Search Report and Written Opinion dated Feb. 19, 2021 pertaining to International application No. PCT/US2020/058829, 14 pgs.

Hai, C. et al. "Roles of ethylene glycol solvent and polymers in preparing uniformly distributed MgO nanoparticles", Journal of Asian Ceramic Societies, [Online] vol. 5, No. 2, Jun. 1, 2017, pp. 176-182.

U.S. Notice of Allowance and Fee(s) Due dated Jan. 5, 2022 pertaining to U.S. Appl. No. 16/701,829, filed Dec. 3, 2019, 8 pages.

Eubank, William R, "Calcination Studies of Magnesium Oxides" Journal of the American Ceramic Society, vol. 34, No. 8, Aug. 1, 1951, pp. 225-229.

Notification of Transmittal of the International Search Report and the Written Opinion of the International Searching Authority, or the Declaration dated May 11, 2022 pertaining to International application No. PCT/US2022/016726 filed Feb. 17, 2022, pp. 1-19.

Maerle, A. A. et al. "Mesoporous MgO: Synthesis, Physico-Chemical, and Catalytic Properties", Russian Journal of Physical Chemistry A, May 21, 2016, pp. 1212-1216, vol. 90, No. 6, Chemical Society, London, GB.

* cited by examiner

METHODS OF PRODUCING ISOMERIZATION CATALYSTS

BACKGROUND

Field

The present disclosure generally relates to catalyst compositions and, more specifically, to isomerization catalysts, methods of making the isomerization catalysts, and methods of using the isomerization catalyst.

Technical Background

In recent years, there has been a dramatic increase in the demand for 1-butene due to applications in the production of polyethylenes, such as high density polyethylene (HDPE) and low density polyethylene (LDPE), and polybutenes. Currently, a majority of the 1-butene produced worldwide is produced by the dimerization of high-value feedstocks, such as ethylene, the dehydrogenation of butane, or separation from low-value $C_4$ feedstocks. These low-value $C_4$ feedstocks may be by-products or effluent streams from steam cracking units, which primarily produce ethylene, Fluid Catalytic Cracking (FCC) units, which primarily produce gasoline, or methyl tertiary butyl ether (MTBE) extraction units. However, these processes cannot respond adequately to the rapid increase in 1-butene demand. As a result, alternative methods to directly produce 1-butene have been developed and, in particular, methods of producing 1-butene from 2-butene-containing feedstocks.

The production of 1-butene from 2-butene-containing feedstocks can be accomplished through the isomerization of the 2-butene to 1-butene. Isomerization of 2-butene to produce 1-butene can better meet the growing demand for 1-butene. Isomerization can be accomplished by contacting 2-butene in the 2-butene-containing feedstock with an isomerization catalyst. However, conventional isomerization catalysts and, as a result, conventional 1-butene production processes are inefficient, often failing to convert a significant portion of 2-butenes and only resulting in a comparatively small 1-butene yield.

SUMMARY

Accordingly, there is an ongoing need for improved isomerization catalysts with increased catalytic activity that, as a result, increases the conversion rate of 2-butene and the yield of 1-butene from a 2-butene isomerization process. The present disclosure is directed to methods of producing an isomerization catalyst through the hydrothermal synthesis of magnesium oxide and acid leaching of the resulting magnesium oxide. The present disclosure is also directed to methods of producing 1-butene from a 2-butene-containing feedstock through isomerization with the isomerization catalyst of the present disclosure. The isomerization catalyst produced by the methods of the present disclosure may have increased thermal stability, which may result in a reduced deactivation rate of the isomerization catalyst when utilized at temperatures sufficient to produce 1-butene from the isomerization of 2-butenes. Additionally, the isomerization catalyst produced by the methods of the present disclosure may have increased weak acidic sites at the catalyst surface enhancing the double-bond-shift isomerization reaction at higher temperatures. Accordingly, the methods of producing 1-butene of the present disclosure may have increased efficiency, an increased conversion rate of 2-butene and greater selectivity to and yield of 1-butene.

According to one or more embodiments of the present disclosure, a method of producing an isomerization catalyst may comprise preparing a catalyst precursor solution comprising at least a magnesium precursor, a hydrolyzing agent, and cetrimonium bromide; hydrothermally treating the catalyst precursor solution to produce a magnesium oxide precipitant; calcining the magnesium oxide precipitant to produce an isomerization catalyst precursor; soaking the isomerization catalyst precursor in an acid solution comprising sulfuric acid to produce a isomerization catalyst precursor precipitant; and calcining the isomerization catalyst precursor precipitant to produce the isomerization catalyst.

According to one or more other embodiments of the present disclosure, an isomerization catalyst is provided and may be produced by a method comprising preparing a catalyst precursor solution comprising at least a magnesium precursor, a hydrolyzing agent, and cetrimonium bromide; hydrothermally treating the catalyst precursor solution to produce a magnesium oxide precipitant; calcining the magnesium oxide precipitant to produce an isomerization catalyst precursor; soaking the isomerization catalyst precursor in an acid solution comprising sulfuric acid to produce a isomerization catalyst precursor precipitant; and calcining the isomerization catalyst precursor precipitant to produce the isomerization catalyst.

According to one or more other embodiments of the present disclosure, a method of producing 1-butene from a 2-butene-containing feedstock may comprise contacting the 2-butene-containing feedstock with an isomerization catalyst to produce an isomerization reaction effluent comprising 1-butene. The isomerization catalyst may be prepared by a method comprising preparing a catalyst precursor solution comprising at least a magnesium precursor, a hydrolyzing agent, and cetrimonium bromide; hydrothermally treating the catalyst precursor solution to produce a magnesium oxide precipitant; calcining the magnesium oxide precipitant to produce an isomerization catalyst precursor; soaking the isomerization catalyst precursor in an acid solution comprising sulfuric acid to produce a isomerization catalyst precursor precipitant; and calcining the isomerization catalyst precursor precipitant to produce the isomerization catalyst.

Additional features and advantages of the technology described in the present disclosure will be set forth in the detailed description that follows and, in part, will be readily apparent to those skilled in the art from the description or recognized by practicing the technology as described in this disclosure.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
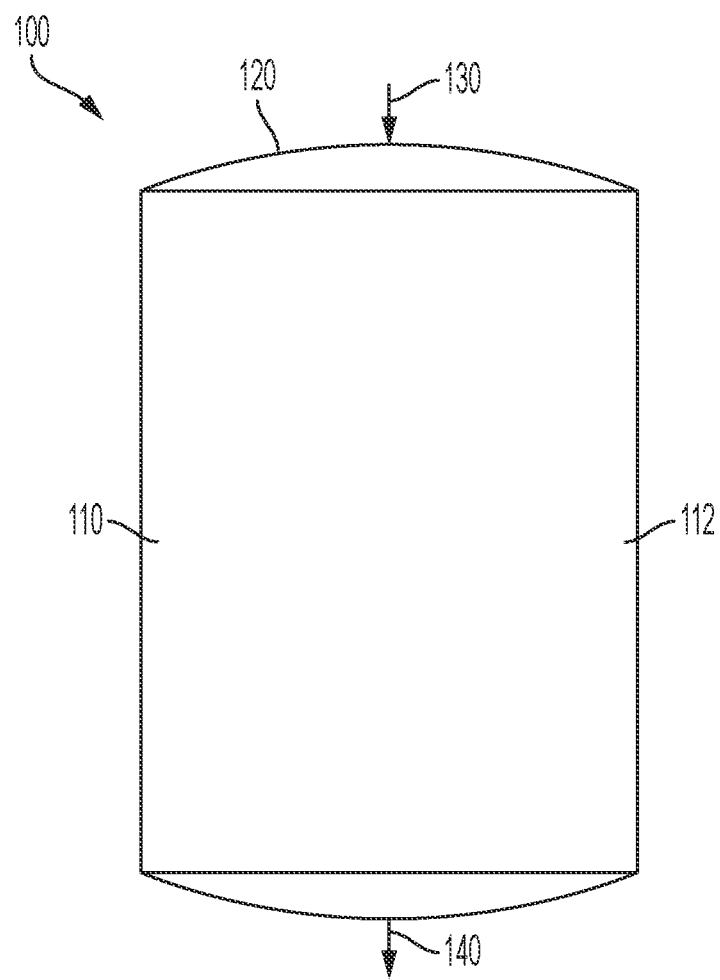
FIG. 1 schematically depicts a fixed bed continuous flow reactor including an isomerization reaction zone, according to one or more embodiments of the present disclosure.
Figure 2:
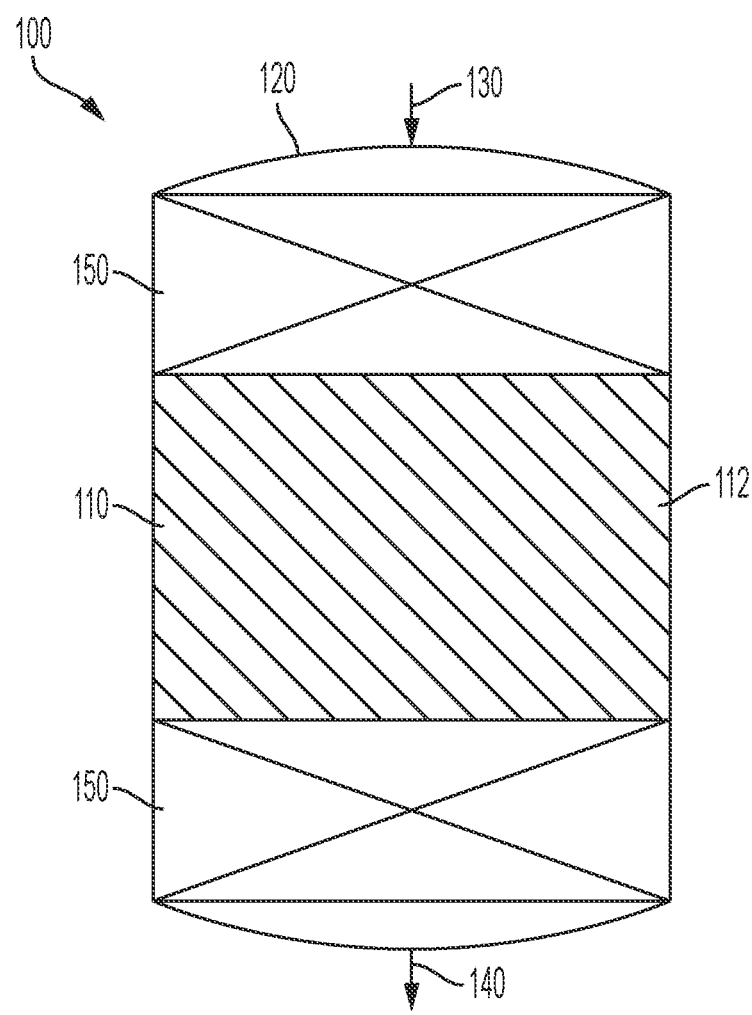
FIG. 2 schematically depicts another fixed bed continuous flow reactor including an isomerization reaction zone, according to one or more embodiments of the present disclosure.

For the purpose of describing the simplified schematic illustrations and descriptions of FIGS. 1 and 2, the numerous valves, temperature sensors, electronic controllers, and the like that may be employed and well-known to a person of ordinary skill in the art are not included. Further, accompanying components that are often included in typical chemical processing operations, carrier gas supply systems, pumps, compressors, furnaces, or other subsystems are not depicted. It should be understood that these components are within the spirit and scope of the present embodiments disclosed. However, operational components, such as those described in the present disclosure, may be added to the embodiments described in the present disclosure.

Arrows in the drawings refer to process streams. However, the arrows may equivalently refer to transfer lines, which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows that do not connect two or more system components may signify a product stream that exits the depicted system or a system inlet stream that enters the depicted system. Product streams may be further processed in accompanying chemical processing systems or may be commercialized as end products.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

Reference will now be made in greater detail to various embodiments, some embodiments of which are illustrated in the accompanying drawings.

DETAILED DESCRIPTION

The present disclosure is directed to an isomerization catalyst and methods of producing the isomerization catalyst. In particular, the present disclosure is directed to methods of producing an isomerization catalyst through the hydrothermal synthesis of magnesium oxide and subsequent acid leaching of the resulting magnesium oxide. The present disclosure is also directed to methods of producing 1-butene from a 2-butene-containing feedstock through isomerization with the isomerization catalyst of the present disclosure. In particular, the present disclosure is directed to methods of producing 1-butene from a 2-butene-containing feedstock that include contacting the 2-butene-containing feedstock with the isomerization catalyst made by the synthesis methods of the present disclosure to produce an isomerization reaction effluent that includes at least 1-butene. The isomerization catalyst produced by the methods of the present disclosure may have increased thermal stability, which may result in a reduced deactivation rate of the isomerization catalyst at temperatures sufficient to produce 1-butene from the isomerization of 2-butene. Additionally, the isomerization catalyst produced by the methods of the present disclosure may have increased weak acidic sites at the catalyst surface enhancing the double-bond-shift isomerization reaction at higher temperatures. Accordingly, systems incorporating the isomerization catalyst produced by the present disclosure may have increased efficiency, an increased conversion rate of 2-butene, and a greater yield of 1-butene.

As used throughout the present disclosure, the term "butene" or "butenes" may refer to compositions comprising one or more than one of 1-butene, trans-2-butene, cis-2-butene, isobutene, or mixtures of these isomers. As used throughout the present disclosure, the term "normal butenes" may refer to compositions comprising one or more than one of 1-butene, trans-2-butene, cis-2-butene, or mixtures of these isomers, and are substantially free of isobutene. As used in the present disclosure, the term "2-butene" may refer to trans-2-butene, cis-2-butene, or a mixture of these two isomers. As used in the present disclosure, the term "substantially free" of a component means less than 1 wt. % of that component in a particular portion of a catalyst, stream, or reaction zone. For example, a composition, which may be substantially free of isobutene, may comprise less than 1 wt. % of isobutene.

As shown in Reaction 1, the isomerization of 2-butene to 1-butene, and the isomerization of 1-butene to 2-butene, is an equilibrium reaction, as denoted by the bi-directional arrows with single heads. The isomerization of 2-butene and 1-butene may be achieved with an isomerization catalyst. As used in the present disclosure, the term "isomerization catalyst" may refer to a catalyst that promotes isomerization of alkenes, including, for example, isomerization of 2-butenes to 1-butene. Referring to Reaction 1, the isomerization reaction is not limited to these reactants and products; however, Reaction 1 provides a simplified illustration of the reaction methodology.

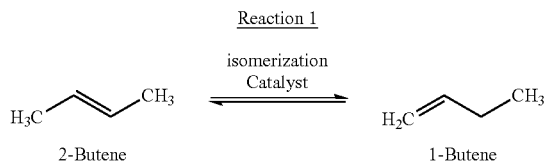

Reaction 1

In operation, a product stream comprising 1-butene may be produced from a feedstock containing 2-butene through isomerization by contacting the feedstock with an isomerization catalyst. Optionally, the isomerization reaction effluent, may be further processed, such as being contacted with a metathesis catalyst, a cracking catalyst, or both, to further utilize the 1-butene produced. The feedstock may comprise 1-butene, trans-2-butene, cis-2-butene, or combinations of these. The feedstock may further comprise other $C_1$-$C_6$ components. The presence of isobutene and other inert gases or non-olefinic hydrocarbons, such as n-butane, in the feedstock do not negatively affect the target isomerization reactions, and the amount of any side products formed as a result of their presence in the feedstock do not affect the overall yield of 1-butene. Although described in the present disclosure in the context of conducting isomerization between 2-butene and 1-butene, it is understood that the isomerization catalysts of the present disclosure and systems and methods of conducting isomerization using the isomerization catalysts may be useful for conducting other isomerization, such as isomerizations between other olefins, or for conducting other functions, such as removing contaminants from a feed stream, for example.

Referring now to FIG. 1, a system for producing 1-butene from a feedstock containing 2-butene is depicted, the system being designated by reference number 100. The system 100 may include an isomerization reaction zone 110 or a plurality of isomerization reaction zones. The one or isomerization reaction zones may be disposed within a single reactor 120 or in multiple reactors, which may be in series or in parallel. As depicted in FIG. 1, a feedstock 130 may be introduced into the reactor 120, and an isomerization reaction effluent 140 may be passed out of the reactor 120. Accordingly, the feedstock 130 may be introduced into the reactor 120, passed through the isomerization reaction zone 110, and passed out of the reactor 120 as the isomerization reaction effluent 140.

As described previously in the present disclosure, the feedstock 130 may comprise 1-butene, cis-2-butene, trans-2-butene, or combinations of these. The feedstock 130 may comprise from 10 wt. % to 60 wt. % 1-butene based on the total weight of the feedstock 130. For example, the feedstock 130 may comprise from 10 wt. % to 50 wt. %, from 10 wt. % to 40 wt. %, from 10 wt. % to 30 wt. %, from 10 wt. % to 20 wt. %, from 20 wt. % to 60 wt. %, from 20 wt. % to 50 wt. %, from 20 wt. % to 40 wt. %, from 20 wt. % to 30 wt. %, from 30 wt. % to 60 wt. %, from 30 wt. % to 50 wt. %, from 30 wt. % to 40 wt. %, from 40 wt. % to 60 wt. %, from 40 wt. % to 50 wt. %, or from 50 wt. % to 60 wt. % 1-butene based on the total weight of the feedstock 130. The feedstock 130 may comprise from 10 wt. % to 100 wt. % 2-butene (that is, cis-2-butene, trans-2-butene, or both) based on the total weight of the feedstock 130. For example, the feedstock 130 may comprise from 10 wt. % to 80 wt. %, from 10 wt. % to 60 wt. %, from 10 wt. % to 40 wt. %, from 10 wt. % to 20 wt. %, from 20 wt. % to 100 wt. %, from 20 wt. % to 80 wt. %, from 20 wt. % to 60 wt. %, from 20 wt. % to 40 wt. %, from 40 wt. % to 100 wt. %, from 40 wt. % to 80 wt. %, from 40 wt. % to 60 wt. %, from 60 wt. % to 100 wt. %, from 60 wt. % to 80 wt. %, or from 80 wt. % to 100 wt. % 2-butene based on the total weight of the feedstock 130. Additionally, the feedstock 130 may be substantially free of ethylene.

The feedstock 130 may comprise a raffinate stream. As used in the present disclosure, the term "raffinate" may refer to the residue $C_4$ stream from a naphtha cracking process or from a gas cracking process when components are removed (the $C_4$ stream typically containing, as its primary components, n-butane, 1-butene, 2-butene, isobutene, and 1,3-butadiene, and optionally some isobutane and said primary components together forming up to 99% or more of the $C_4$ stream). The feedstock 130 may comprise a raffinate-1 stream. As used in the present disclosure, the term "raffinate-1" may refer to the $C_4$ residual obtained after separation of 1,3-butadiene from a raffinate stream, and comprises mainly 2-butene, 1-butene, and isobutene, which may make up greater than or equal to 55 wt. % of the raffinate-1 stream. For example, the raffinate-1 stream may comprise from 10 wt. % to 30 wt. % of 2-butene, from 25 wt. % to 50 wt. % of 1-butene, and from 20 wt. % to 50 wt. % isobutene, based on the total weight of the raffinate-1 stream. The feedstock 130 may comprise a raffinate-2 stream. As used in the present disclosure, the term "raffinate-2" may refer to the $C_4$ residual obtained after separation of 1,3-butadiene and isobutene from a raffinate stream, and comprises mainly 2-butene, 1-butene, and n-butane, which may make up greater than or equal to 45 wt. % of the raffinate-2 stream. For example, the raffinate-2 stream may comprise from 20 wt. % to 60 wt. % of 2-butene, from 10 wt. % to 60 wt. % of 1-butene, and from 15 wt. % to 25 wt. % n-butane, based on the total weight of the raffinate-2 stream. The feedstock 130 may comprise a raffinate-3 stream. As used in the present disclosure, the term "raffinate-3" may refer to the $C_4$ residual obtained after separation of 1,3-butadiene, isobutene, and 1-butene from the $C_4$ raffinate stream, and comprises mainly 2-butene, n-butane, and unseparated 1-butene, which may make up greater than or equal to 40 wt. % of the raffinate-3 stream. For example, the raffinate-3 stream may comprise from 30 wt. % to 70 wt. % of 2-butene and from 10 wt. % to 30 wt. % of n-butane, based on the total weight of the raffinate-3 stream.

The isomerization reaction zone 110 may be maintained at an isomerization reaction temperature sufficient to promote the isomerization reactions between 2-butene and 1-butene in the feedstock 130. The isomerization reaction temperature may be from 300 degrees Celsius (° C.) to 600° C. For example, the isomerization reaction temperature may be from 300° C. to 550° C., from 300° C. to 500° C., from 350° C. to 600° C., from 350° C. to 550° C., from 350° C. to 500° C., from 400° C. to 600° C., from 400° C. to 550° C., or from 400° C. to 500° C. These temperature ranges may be sufficient to promote the isomerization reactions and, in particular, may be sufficient to promote the isomerization of 2-butene to 1-butene. Without being bound by any particular theory, it is believed that these temperature ranges may shift the equilibrium of the isomerization reactions between 2-butene and 1-butene, such that the production of 1-butene is favored. Conversely, temperatures less than these temperature ranges may shift the equilibrium of the isomerization reactions between 2-butene and 1-butene, such that the production of 2-butene is favored. Accordingly, these temperature ranges may increase the yield of 1-butene by system 100.

Referring still to FIG. 1, the isomerization reaction zone 110 of the system 100 may include an isomerization catalyst 112. The isomerization catalyst 112 may be a magnesium oxide (MgO) catalyst subjected to acid leaching in accordance with the present disclosure. The isomerization catalyst 112 may promote equilibration of the isomerization reactions between the 2-butene and 1-butene in the feedstock 130. When the feedstock 130 has a concentration of 2-butene greater than the equilibration concentration of 2-butene, the isomerization catalyst 112 may isomerize at least a portion of the 2-butene to 1-butene. Conversely, when the feedstock 130 has a concentration of 1-butene greater than the equilibrium concentration of 1-butene, the isomerization catalyst 112 may isomerize at least a portion of the 1-butene to 2-butene. As described previously, the isomerization catalyst 112 may also shift the equilibrium of the isomerization reactions between 2-butene and 1-butene, such that the production of 1-butene is favored at equilibrium, or such that the production of 2-butene is favored at equilibrium, based on the operating conditions of the system 100. For example, at temperatures greater than 300° C., the isomerization catalyst 112 may shift the equilibrium of the isomerization reactions between 2-butene and 1-butene, such that the production of 1-butene is favored at equilibrium. Conversely, at temperatures less than 300° C., the isomerization catalyst 112 may shift the equilibrium of the isomerization reactions between 2-butene and 1-butene, such that the production of 2-butene is favored at equilibrium. The isomerization reaction zone 110 may produce an isomerization effluent that may comprise 1-butene, cis-2-butene, trans-2-butene, or combinations of these.

As described previously in the present disclosure, commercially-available magnesium oxide catalysts may have poor catalytic activity, inferior thermal stability, or both, which may result in a decreased yield of 1-butene. Accordingly, the isomerization catalyst 112 of the present disclosure may be prepared using a hydrothermal synthesis method and subsequent acid leaching of the resulting magnesium oxide. The resulting isomerization catalyst 112 may have increased thermal stability and catalytic activity compared to commercially-available magnesium oxide catalysts. During hydrothermal synthesis, the isomerization catalyst may be synthesized from the reaction of a magnesium precursor, such as but not limited to magnesium nitrate hexahydrate, a hydrolyzing agent, such as but not limited to urea, and a surfactant, such as cetrimonium bromide (CTAB), in an aqueous solution to form a catalyst precursor solution. The catalyst precursor solution may then be hydrothermally treated in order to produce a magnesium oxide precipitant. The magnesium oxide resulting from the reaction taking place during the hydrothermal treatment may precipitate out of the catalyst precursor solution as a white solid, which may then be separated, washed, dried, and calcined to form an isomerization catalyst precursor. It will be appreciated that the inclusion of a surfactant may increase the surface area and cumulative volume of pores and reduce the average particle size of the resulting magnesium oxide precipitant. The isomerization catalyst precursor may then be further processed by soaking the isomerization catalyst precursor in an acid solution comprising sulfuric acid to produce a isomerization catalyst precursor precipitant, which may then be separated, dried, and calcined to form the isomerization catalyst.

As described previously in the present disclosure, the catalyst precursor solution used in the hydrothermal synthesis may comprise a magnesium precursor and a hydrolyzing agent. The magnesium precursor may be selected from one or more of magnesium nitrate hexahydrate, magnesium acetate tetrahydrate, and magnesium chloride tetrahydrate. The hydrolyzing agent may be selected from one or more of urea, a diamine, such as ethylene diamine, and ammonium hydroxide. The catalyst precursor solution used in the hydrothermal synthesis may comprise the magnesium precursor and the hydrolyzing agent in a molar ratio of from 1:10 to 1:1. For example, the catalyst precursor solution used in the hydrothermal synthesis may comprise the magnesium precursor and the hydrolyzing agent in a molar ratio of from 1:10 to 1:2, from 1:10 to 1:3, from 1:10 to 1:4, from 1:10 to 1:5, from 1:10 to 1:6, from 1:10 to 1:7, from 1:10 to 1:8, from 1:10 to 1:9, from 1:9 to 1:1, from 1:9 to 1:2, from 1:9 to 1:3, from 1:9 to 1:4, from 1:9 to 1:5, from 1:9 to 1:6, from 1:9 to 1:7, from 1:9 to 1:8, from 1:8 to 1:1, from 1:8 to 1:2, from 1:8 to 1:3, from 1:8 to 1:4, from 1:8 to 1:5, from 1:8 to 1:6, from 1:8 to 1:7, from 1:7 to 1:1, from 1:7 to 1:2, from 1:7 to 1:3, from 1:7 to 1:4, from 1:7 to 1:5, from 1:7 to 1:6, from 1:6 to 1:1, 1:6 to 1:2, from 1:6 to 1:3, from 1:6 to 1:4, from 1:6 to 1:5, from 1:5 to 1:1, from 1:5 to 1:2, from 1:5 to 1:3, from 1:5 to 1:4, from 1:4 to 1:1, from 1:4 to 1:2, from 1:4 to 1:3, from 1:3 to 1:1, from 1:3 to 1:2, or from 1:2 to 1:1. Without being bound by any particular theory, it is believed that the hydrolyzing agent may increase the yield of magnesium oxide during the hydrothermal synthesis by improving the seeding effect and crystallization of magnesium oxide during precipitation. For example, when catalyst precursor solution used in the hydrothermal synthesis comprises the magnesium precursor and the hydrolyzing agent in a molar ratio less than 1:10, the yield of the magnesium oxide, and the isomerization catalyst, may be reduced. This reduced yield may render the process unsuitable for the production of the isomerization catalyst on an industrial scale.

As described previously in the present disclosure, the catalyst precursor solution used in the hydrothermal synthesis may further comprise cetrimonium bromide. The catalyst precursor solution used in the hydrothermal synthesis may comprise the magnesium precursor and cetrimonium bromide in a molar ratio of from 1:0.1 to 1:0.01. For example, the catalyst precursor solution used in the hydrothermal synthesis may comprise the magnesium precursor and cetrimonium bromide in a molar ratio of from 1:0.1 to 1:0.02, from 1:0.1 to 1:0.03, from 1:0.1 to 1:0.04, from 1:0.1 to 1:0.05, from 1:0.1 to 1:0.06, from 1:0.1 to 1:0.07, from 1:0.1 to 1:0.08, from 1:0. 1 to 1:0.09, from 1:0.09 to 1:0.01, from 1:0.09 to 1:0.02, from 1:0.09 to 1:0.03, from 1:0.09 to 1:0.04, from 1:0.09 to 1:0.05, from 1:0.09 to 1:0.06, from 1:0.09 to 1:0.07, from 1:0.09 to 1:0.08, from 1:0.08 to 1:0.01, from 1:0.08 to 1:0.02, from 1:0.08 to 1:0.03, from 1:0.08 to 1:0.04, from 1:0.08 to 1:0.05, from 1:0.08 to 1:0.06, from 1:0.08 to 1:0.07, from 1:0.07 to 1:0.01, from 1:0.07 to 1:0.02, from 1:0.07 to 1:0.03, from 1:0.07 to 1:0.04, from 1:0.07 to 1:0.05, from 1:0.07 to 1:0.06, from 1:0.06 to 1:0.01, 1:0.06 to 1:0.02, from 1:0.06 to 1:0.03, from 1:0.06 to 1:0.04, from 1:0.06 to 1:0.05, from 1:0.05 to 1:0.01, from 1:0.05 to 1:0.02, from 1:0.05 to 1:0.03, from 1:0.05 to 1:0.04, from 1:0.04 to 1:0.01, from 1:0.04 to 1:0.02, from 1:0.04 to 1:0.03, from 1:0.03 to 1:0.01, from 1:0.03 to 1:0.02, or from 1:0.02 to 1:0.01. Without being bound by any particular theory, it is believed that cetrimonium bromide may act as a surface directing agent during hydrothermal synthesis, affecting the mesoporosity of the resulting magnesium oxide and, as a result, the surface area and pore volume of the isomerization catalyst. For example, when the catalyst precursor solution used in the hydrothermal synthesis comprises the magnesium precursor and cetrimonium bromide in a molar ratio less than 1:0.1, the surface area and pore volume of the resulting isomerization catalyst may be reduced, resulting in a decrease in catalytic activity.

The pH of the catalyst precursor solution used in the hydrothermal synthesis may be adjusted such that the catalyst precursor solution is more acidic or more basic. The pH of the catalyst precursor solution used in the hydrothermal synthesis may be adjusted such that the pH of the catalyst precursor solution is from 8 to 12. For example, the pH of the catalyst precursor solution used in the hydrothermal synthesis may be adjusted such that the pH of the catalyst precursor solution is from 9 to 12, from 10 to 12, or from 11 to 12. Without being bound by any particular theory, it is believed that the pH of the catalyst precursor solution may affect the yield of the isomerization catalyst, the morphology of the isomerization catalyst, or both. For example, acidic or basic catalyst precursor solutions may result in the increased precipitation of magnesium oxide during hydrothermal synthesis and, as a result, increase the yield of the isomerization catalysts. Additionally, the morphology of the isomerization catalyst, which may increase or decrease the catalytic activity, may be determined by the presence of anionic and cationic species within the catalyst precursor solution. In particular, the anionic and cationic species, the concentration of which increases with the acidity or basicity of the catalyst precursor solution, may be responsible for stearic hindrance during hydrothermal synthesis. Such stearic hindrance may affect the morphology of the resulting magnesium oxide and, as a result, increase the catalytic activity of the isomerization catalyst.

As described previously in the present disclosure, the catalyst precursor solution may be hydrothermally treated in order to produce the magnesium oxide precipitant. The hydrothermal treatment may comprise heating the catalyst precursor solution. The heating of the catalyst precursor solution may be conducted in a pressure vessel, such as an autoclave. The hydrothermal treatment of the catalyst precursor solution may comprise heating the catalyst precursor solution to a temperature sufficient to cause the reaction of the magnesium precursor and the hydrolyzing agent, resulting in the precipitation of magnesium oxide from the catalyst precursor solution. The hydrothermal treatment of the catalyst precursor solution may comprise heating the catalyst precursor solution to a temperature of from 100° C. to 140° C. For example, the hydrothermal treatment of the catalyst precursor solution may comprise heating the aqueous solution to a temperature of from 100° C. to 135° C., from 100° C. to 130° C., from 100° C. to 125° C., from 100° C. to 120° C., from 100° C. to 115° C., from 100° C. to 110° C., from 100° C. to 105° C., from 105° C. to 140° C., from 105° C. to 135° C., from 105° C. to 130° C., from 105° C. to 125° C., from 105° C. to 120° C., from 105° C. to 115° C., from 105° C. to 110° C., from 110° C. to 140° C., from 110° C. to 135° C., from 110° C. to 130° C., from 110° C. to 125° C., from 110° C. to 120° C., from 110° C. to 115° C., from 115° C. to 140° C., from 115° C. to 135° C., from 115° C. to 130° C., from 115° C. to 125° C., from 115° C. to 120° C., from 120° C. to 140° C., from 120° C. to 135° C., from 120° C. to 130° C., from 120° C. to 125° C., from 125° C. to 140° C., from 125° C. to 135° C., from 125° C. to 130° C., from 130° C. to 140° C., from 130° C. to 135° C., or from 135° C. to 140° C.

The hydrothermal treatment of the catalyst precursor solution may comprise heating the catalyst precursor solution for an amount of time sufficient to cause the reaction of the magnesium precursor and the hydrolyzing agent, resulting in the precipitation of magnesium oxide from the catalyst precursor solution. In embodiments, the hydrothermal treatment of the catalyst precursor solution may comprise heating the catalyst precursor solution for a duration of from 48 hours to 96 hours. For example, the hydrothermal treatment of the catalyst precursor solution may comprise heating the catalyst precursor solution for a duration of from 48 hours to 84 hours, from 48 hours to 72 hours, from 48 hours to 60 hours, from 60 hours to 96 hours, from 60 hours to 84 hours, from 60 hours to 72 hours, from 72 hours to 96 hours, from 72 hours to 84 hours, or from 84 hours to 96 hours.

As described previously in the present disclosure, after hydrothermal treatment the precipitated magnesium oxide precipitant may be separated, washed, dried, and calcined to produce the isomerization catalyst precursor. Without being bound by any particular theory, it is believed that the calcination of the magnesium oxide precipitant to produce the isomerization catalyst precursor may activate the reaction sites for butene isomerization. Magnesium oxide, which forms the isomerization catalyst precursor, is generally basic in nature and the basicity of the magnesium oxide may be influenced by the calcination temperature and process. Calcination conditions may influence the strength and quantity of basic reaction sites in the magnesium oxide of the isomerization catalyst precursor which is formed. Selection of the appropriate calcination temperature may enhance the number and strength of the basic sites in the magnesium oxide, thus, enhancing the isomerization performance of the isomerization catalyst 112 ultimately generated from the isomerization catalyst precursor. The "calcination temperature" is a target average temperature to which the magnesium oxide precipitant is heated and at which the magnesium oxide precipitant is calcined over a period of time during the calcination process. The "ramping rate," as used in the present disclosure, is a rate at which the temperature of the magnesium oxide precipitant is increased from a starting temperature to the calcination temperature. The magnesium oxide precipitant may be placed in the calcination oven and the temperature of the calcination oven may be increased at the ramping rate to the calcination temperature. Then, the magnesium oxide precipitant may be maintained at the calcination temperature for a predetermined period of time. At the end of the predetermined period of time, the calcined magnesium oxide forming an isomerization catalyst precursor may be allowed to slowly cool down to ambient temperature. Optionally, the isomerization catalyst precursor may be calcined a second time. The calcination temperature, ramping rate, and duration of the second calcination process may each be the same or different from the calcination temperature, ramping rate, and duration of the first calcination process.

The magnesium oxide precipitant may be calcined to form the isomerization catalyst precursor in a calcination oven at a calcination temperature of from 450° C. to 650° C. For example, the magnesium oxide precipitant may be calcined in a calcination oven at a calcination temperature of from 450° C. to 600° C., from 450° C. to 550° C., from 450° C. to 500° C., from 500° C. to 650° C., from 500° C. to 600° C., from 500° C. to 550° C., from 550° C. to 650° C., from 550° C. to 600° C., or from 600° C. to 650° C. The ramping rate of the calcination process may be from 1 degree Celsius per minute (° C./min) to 4° C./min. For example, the ramping rate of the calcination process may be from 1° C./min to 3° C./min, from 1° C./min to 2.5° C./min, from 1° C./min to 2° C./min, from 1.5° C./min to 2° C./min, from 1.5° C./min to 4° C./min, from 1.5° C./min to 3° C./min, from 1.5° C./min to 2.5° C./min, from 1.5° C./min to 2° C./min, from 2° C./min to 4° C./min, from 2° C./min to 3° C./min, from 2° C./min to 2.5° C./min, from 2.5° C./min to 4° C./min, from 2.5° C./min to 3° C./min, or from 3° C./min to 4° C./min. The magnesium oxide precipitant may be calcined in the calcination oven for a duration of from 1 hour to 10 hours. For example, the magnesium oxide precipitant may be calcined in the calcination oven for a duration of from 1 hour to 8 hours, from 1 hour to 6 hours, from 1 hour to 4 hours, from 1 hour to 2 hours, from 2 hours to 10 hours, from 2 hours to 8 hours, from 2 hours to 6 hours, from 2 hours to 4 hours, from 4 hours to 10 hours, from 4 hours to 8 hours, from 4 hours to 6 hours, from 6 hours to 10 hours, from 6 hours to 8 hours, or from 8 hours.

As described previously in the present disclosure, the isomerization catalyst precursor may be soaked in an acid solution comprising sulfuric acid to produce the isomerization catalyst precursor precipitant. Soaking the isomerization catalyst precursor in an acid solution leaches components out of the isomerization catalyst precursor thereby introducing acidic sites to the existing basic magnesium oxide surface of the isomerization catalyst precursor. In the acid leaching process, the MgO spatial pores increase in size. This phenomenon is the result of a redox reaction between acid and base components which results in the creation of voids and the altering of the structural properties of the MgO.

It is noted, without wishing to be bound by theory, that acids having strong Cl and $NO_3$ ions, such as in HCl and $HNO_3$, are believed to deactivate the MgO of the isomerization catalyst precursor at a faster rate. As a result, the disclosed sulfuric acid ($H_2SO_4$) is believed to provide superior leaching performance compared to other acids.

In one or more embodiments, the acid solution comprising sulfuric acid may be a 0.5 molar (M) to 1.2M sulfuric acid solution. For example, the acid solution may be a 0.5M to 1.1M sulfuric acid solution, 0.65M to 1.2M sulfuric acid solution, 0.65M to 1.1M sulfuric acid solution, 0.8M to 1.2M sulfuric acid solution, or 0.8M to 1.1M sulfuric acid solution. It is noted that a higher percentage of sulfuric acid solution decreases the isomerization capacity of the resulting catalyst. It will be appreciated that based on the moles of the MgO molecule, the $H_2SO_4$ quantity to treat the entire catalyst may be quantified. Specifically, for each mole of MgO only 1-5% (0.65 to 1.25 M) of $H_2SO_4$ molar solution is needed to treat the entire catalyst.

In one or more embodiments, the isomerization catalyst precursor is soaked in the acid solution comprising sulfuric acid for a period of 5 to 30 minutes. For example, the isomerization catalyst precursor may be soaked in the acid solution comprising sulfuric acid for a period of 5 to 25 minutes, 5 to 20 minutes, 10 to 30 minutes, 10 to 25 minutes, 10 to 20 minutes, or approximately 15 minutes. It is believed that extended soaking time may result in deactivation of the catalytic activity of the resulting catalyst. Conversely, it is believed that insufficient soaking time may not result in sufficient treatment of the MgO and insufficient pore formation.

In one or more embodiments, the isomerization catalyst precursor precipitant formed from soaking the isomerization catalyst precursor in the acid solution comprising sulfuric acid may be filtered from the acid solution through any method known to those skilled in the art. For example, the isomerization catalyst precursor precipitant may be filtered from the acid solution via a vacuum filtration method.

The isomerization catalyst precursor precipitant separated from the acid solution may be dried. In one or more embodiments, the isomerization catalyst precursor precipitant may be dried through exposure to ambient air at ambient temperature through natural evaporative drying. In one or more embodiments, the isomerization catalyst precursor precipitant may be dried with vacuum drying. For example, the isomerization catalyst precursor precipitant may be placed in a vacuum oven at approximately 80° C. to draw out and expedite evaporation of the acid solution to leave a dried powder of the isomerization catalyst precursor precipitant. It will be appreciated that embodiments comprising the natural evaporative drying and embodiments comprising the vacuum drying may be combined to generate one or more embodiments with a hybrid drying method.

The isomerization catalyst precursor precipitant may be calcined to form the isomerization catalyst in a calcination oven at a calcination temperature of from 450° C. to 650° C. For example, the isomerization catalyst precursor precipitant may be calcined in a calcination oven at a calcination temperature of from 450° C. to 600° C., from 450° C. to 550° C., from 450° C. to 500° C., from 500° C. to 650° C., from 500° C. to 600° C., from 500° C. to 550° C., from 550° C. to 650° C., from 550° C. to 600° C., or from 600° C. to 650° C. The ramping rate of the calcination process may be from 1 degree ° C./min to 4° C./min. For example, the ramping rate of the calcination process may be from 1° C./min to 3° C./min, from 1° C./min to 2.5° C./min, from 1° C./min to 2° C./min, from 1.5° C./min to 2° C./min, from 1.5° C./min to 4° C./min, from 1.5° C./min to 3° C./min, from 1.5° C./min to 2.5° C./min, from 1.5° C./min to 2° C./min, from 2° C./min to 4° C./min, from 2° C./min to 3° C./min, from 2° C./min to 2.5° C./min, from 2.5° C./min to 4° C./min, from 2.5° C./min to 3° C./min, or from 3° C./min to 4° C./min. The isomerization catalyst precursor precipitant may be calcined in the calcination oven for a duration of from 1 hour to 10 hours. For example, the isomerization catalyst precursor precipitant may be calcined in the calcination oven for a duration of from 1 hour to 8 hours, from 1 hour to 6 hours, from 1 hour to 4 hours, from 1 hour to 2 hours, from 2 hours to 10 hours, from 2 hours to 8 hours, from 2 hours to 6 hours, from 2 hours to 4 hours, from 4 hours to 10 hours, from 4 hours to 8 hours, from 4 hours to 6 hours, from 6 hours to 10 hours, from 6 hours to 8 hours, or from 8 hours.

The isomerization catalyst 112 resulting from the process of the present disclosure may have a surface area of less than 100 square meters per gram ($m^2/g$), as determined by the Brunauer Emmett-Teller (BET) method. For example, the isomerization catalyst 112 may have a surface area of from 1 $m^2/g$ to 100 $m^2/g$, from 20 $m^2/g$ to 100 $m^2/g$, from 400 $m^2/g$ to 100 $m^2/g$, from 30 $m^2/g$ to 80 $m^2/g$, from 40 $m^2/g$ to 80 $m^2/g$, from 40 $m^2/g$ to 60 $m^2/g$, or from 35 $m^2/g$ to 55 $m^2/g$, as determined by the BET method. For comparison, in one or more embodiments, the isomerization catalyst precursor may have a surface area of 100 $m^2/g$ to 300 $m^2/g$, as determined by the BET method. Such demonstrates a substantial reduction in the surface area of the isomerization catalyst 112 as a result of the acid leaching of the isomerization catalyst precursor.

The isomerization catalyst 12 resulting from the process of the present disclosure may have a cumulative pore volume of from 0.05 cubic centimeters per gram ($cm^3/g$) to 0.30 $cm^3/g$, as determined by the Barrett, Joyner, and Halenda (BJH) method. For example, the isomerization catalyst 112 may have a cumulative pore volume of from 0.05 $cm^3/g$ to 0.26 $cm^3/g$, from 0.05 $cm^3/g$ to 0.22 $cm^3/g$, from 0.05 $cm^3/g$ to 0.18 $cm^3/g$, from 0.05 $cm^3/g$ to 0.16 $cm^3/g$, from 0.10 $cm^3/g$ to 0.26 $cm^3/g$, from 0.10 $cm^3/g$ to 0.22 $cm^3/g$, from 0.10 $cm^3/g$ to 0.18 $cm^3/g$, from 0.10 $cm^3/g$ to 0.16 $cm^3/g$, from 0.12 $cm^3/g$ to 0.22 $cm^3/g$, from 0.12 $cm^3/g$ to 0.18 $cm^3/g$, from 0.12 $cm^3/g$ to 0.16 $cm^3/g$, from 0.14 $cm^3/g$ to 0.22 $cm^3/g$, from 0.14 $cm^3/g$ to 0.18 $cm^3/g$, or from 0.14 $cm^3/g$ to 0.16 $cm^3/g$, as determined by the BJH method.

The isomerization catalyst 112 resulting from the process of the present disclosure may have an average pore width of from 6 nanometers (nm) to 10 nm, as determined by the BJH method. For example, the isomerization catalyst 112 may have an average pore width of 6 nm to 9 nm, 6 nm to 8 nm, 7 nm to 10 nm, 7 nm to 9 nm, or approximately 8 nm.

The isomerization catalyst 112 resulting from the process of the present disclosure may have an average particle size of from 20 nm to 30 nm, as calculated by the Scherrer equation. For example, the isomerization catalyst 112 may have an average particle size of 20 nm to 26 nm, 20 nm to 24 nm, 22 nm to 30 nm, 22 nm to 26 nm, 22 nm to 24 nm or approximately 23.5 nm.

The isomerization catalyst 112 having these properties (that is, the previously described surface area, cumulative pore volume, average pore width, and average particle size) may have increased catalytic activity and thermal stability compared to commercially-available magnesium oxide catalysts. As a result, the system 100 comprising the isomerization catalyst 112 may have an increased 1-butene yield compared to a system utilizing a conventional magnesium oxide catalyst.

Referring now to FIG. 2, in embodiments, a fluid/solid separator 150 may be disposed downstream of the isomerization reaction zone 110, upstream of the isomerization reaction zone 110, or both. As used in the present disclosure, the term "fluid/solid separator" may refer to a fluid permeable barrier between catalyst beds that reduces or prevents solid catalyst particles in one catalyst bed from migrating from the reaction zone, while allowing for reactants and products to move through the separator. The fluid/solid separator 150 may be chemically inert and generally makes no contribution to the reaction chemistry. Inserting the fluid/solid separator 150 upstream or downstream of the isomerization reaction zone 110 may maintain the isomerization catalyst 112 in the isomerization reaction zone 110, and improve the isothermal stability of the isomerization reactions, which may lead to the decreased production of undesired by-products and increased yield of 1-butene.

Referring again to FIG. 1, various operating conditions are contemplated for contacting the feedstock 130 with the isomerization catalyst 112 in the isomerization zone 110. In embodiments, the feedstock 130 may contact the isomerization catalyst 112 in the isomerization zone 110 at a weight hourly space velocity (WHSV) of from 1 per hour ($h^{-1}$) to 5 $h^{-1}$. For example, the feedstock 130 may contact the isomerization catalyst 112 in the isomerization zone 110 at a space hour velocity of 1 $h^{-1}$ to 3 $h^{-1}$, 2 $h^{-1}$ to 5 $h^{-1}$, 2 $h^{-1}$ to 3 $h^{-1}$, 2.2 $h^{-1}$ to 2.6 $h^{-1}$, or approximately 2.4 $h^{-1}$. Furthermore, the feedstock 130 may contact the isomerization catalyst 112 in the isomerization zone 110 at a pressure of from 0.5 bar to 2 bars. For example, the feedstock 130 may contact the isomerization catalyst 112 in the isomerization zone 110 at a pressure of from 0.5 bar to 1.5 bars, from 0.5 bar to 1.25 bars, from 0.75 bars to 2 bars, from 0.75 bars to 1.5 bars, or from 0.75 bars to 1.2 bars. The feedstock 130 may also contact the isomerization catalyst 112 in the isomerization zone 110 at atmospheric pressure (approximately 1.01 bars).

Optionally, prior to the introduction of the feedstock 130 to the system 100, the isomerization catalyst 112 may be pretreated. For example, the isomerization catalyst 112 in the system 100 may be pretreated by passing a heated gas stream through the isomerization catalyst 112 for a pretreatment period. The gas stream may include one or more of an oxygen-containing gas, nitrogen gas ($N_2$), carbon monoxide (CO), hydrogen gas ($H_2$), a hydrocarbon gas, air, other inert gas, or combinations of these gases. The temperature of the heated gas stream may be from 545° C. to 570° C., from 550° C. to 570° C., from 550° C. to 560° C., from 550° C. to 555° C., from 545° C. to 565° C., from 545° C. to 560° C., from 545° C. to 555° C., from 545° C. to 550° C., or approximately 550° C. The pretreatment period may be from 20 hours to 30 hours, 20 hours to 26 hours, 22 hours to 30 hours, 22 hours to 26 hours, 23 hours to 25 hours, or approximately 24 hours. For example, the isomerization catalyst 112 in the system 100 may be pretreated with nitrogen gas at a temperature of 550° C. for a pretreatment period of approximately 24 hours before introducing the feedstock 130.

EXAMPLES

The various embodiments of isomerization catalysts, methods of making the isomerization catalysts, and methods of using the isomerization catalyst in the production of 1-butene will be further clarified by the following examples. The examples are illustrative in nature, and should not be understood to limit the subject matter of the present disclosure.

Comparative Example 1-Hydrothermal Synthesis of MgO

An isomerization catalyst was prepared using hydrothermal synthesis. In particular, 18.02 grams (g) of urea (Alfa Aesar) and 15.39 g of magnesium nitrate hexahydrate (Mg$(NO_3)_2 \cdot 6H_2O$) (99%, Sigma-Aldrich) were dissolved in 100 milliliters (mL) of deionized water (DI water) and rapidly stirred at room temperature for 1 hour to form a first solution. Cetrimonium bromide (CTAB) (Sigma Aldrich, >98% purity) was then added to the first solution such that the molar ratio of magnesium to cetrimonium bromide in the first solution was 1:0.03, and the first solution was stirred at room temperature for 2 hours to form a catalyst precursor solution. The pH of the catalyst precursor solution was then adjusted to a pH of 11 by the dropwise addition of concentrated ammonium (28-30% $NH_3$ basis). The catalyst precursor solution was then transferred to an autoclave and placed in an oven at 120° C. for 72 hours at a ramp rate of 1 degree Celsius per minute (° C./min). The resulting magnesium oxide precipitants were then filtered from the solution via vacuum filtration (Whatman filter paper, 400), dried overnight at room temperature, and then dried in a vacuum oven at 80° C. for 24 hours to form a dried magnesium oxide precipitant. The dried magnesium oxide precipitant was then calcined in a calcination oven under air at a ramping rate of 1° C./min until the dried magnesium oxide precipitant attained a temperature of 550° C. The dried magnesium oxide precipitant was then maintained in the calcination oven at a temperature of 550° C. for 5 hours to form the isomerization catalyst precursor in accordance with the present disclosure. Following calcination, the isomerization catalyst precursor was maintained in the calcination oven and allowed to slowly cool to room temperature. The isomerization catalyst precursor prepared according to the above-described method is referred to subsequently as the catalyst of Comparative Example 1.

Inventive Example 2— Sulfuric Acid Leached Hydrothermally Synthesized MgO

The isomerization catalyst precursor of Comparative Example 1 was further leached with a sulfuric acid solution. Specifically, the isomerization catalyst precursor of Comparative Example 1 was soaked in 1M $H_2SO_4$ for 15 minutes. The resulting white precipitants after the acid solution soaking were then filtered from the solution via vacuum filtration (Whatman filter paper, 400), dried overnight at room temperature, and then dried in a vacuum oven at 80° C. for 24 hours to form an isomerization catalyst precursor precipitant in accordance with the present disclosure. The isomerization catalyst precursor precipitant was then calcined in a calcination oven under air at a ramping rate of 1° C./min until the isomerization catalyst precursor precipitant attained a temperature of 550° C. The isomerization catalyst precursor precipitant was then maintained in the calcination oven at a temperature of 550° C. for 5 hours to form the isomerization catalyst in accordance with the present disclosure. Following calcination, the isomerization catalyst was maintained in the calcination oven and allowed to slowly cool to room temperature. The isomerization catalyst prepared according to the above-described method is referred to subsequently as the catalyst of Inventive Example 2.

Comparative Example 3— Hydrochloric Acid Leached Hydrothermally Synthesized MgO

The isomerization catalyst precursor of Comparative Example 1 was further leached with a sulfuric acid solution. Specifically, the isomerization catalyst precursor of Comparative Example 1 was soaked in 1M HCl for 15 minutes. The resulting white precipitants after the acid solution soaking were then further processed according to the same methods as Inventive Example 2. The isomerization catalyst prepared according to the above-described method is referred to subsequently as the catalyst of Comparative Example 3.

Comparative Example 4—Commercially-Available Magnesium Oxide Catalyst

An isomerization catalyst was prepared from a magnesium oxide base material, commercially available from Sigma Aldrich. The commercially-available magnesium oxide was dried overnight in a vacuum oven at 90° C. to form an isomerization catalyst. The isomerization catalyst was then calcined in a calcination oven under air at a ramping rate of 1° C./min until the isomerization catalyst attained a temperature of 550° C. The isomerization catalyst was then maintained in the calcination oven at a temperature of 550° C. for 5 hours. Following calcination, the isomerization catalyst was maintained in the calcination oven and allowed to slowly cool to room temperature. The isomerization catalyst prepared according to the above-described method is referred to subsequently as the catalyst of Comparative Example 4.

Evaluation of Isomerization Catalyst Structures

Figure 3:
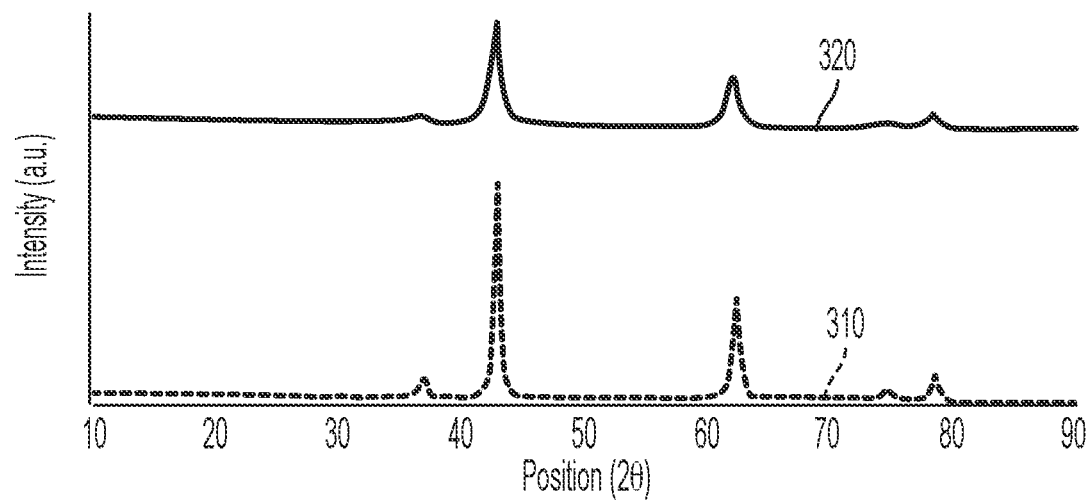
FIG. 3 graphically depicts the X-ray diffraction (XRD) profiles of isomerization catalysts, according to one or more embodiments of the present disclosure.

The crystallographic structures of the catalysts of Examples 1 and 2 were obtained from the measured XRD profiles of the catalysts. The XRD profiles of the catalyst of Comparative Example 1 (310) and the catalyst of Inventive Example 2 (320) are depicted in FIG. 3. The diffraction peaks corresponding to the cubic structure of magnesium oxide in a single phase may be observed in FIG. 3 at 2 Theta (2θ)=36 degrees (°), 42°, 62°, 74°, and 78° for all examples. A comparison of the XRD patterns between Comparative Example 1 and Inventive Example 2 demonstrates that after the acid leaching procedure, the intensity of MgO peaks was reduced. Such reduction is indicative of distortion in the MgO structure.

Figure 4:
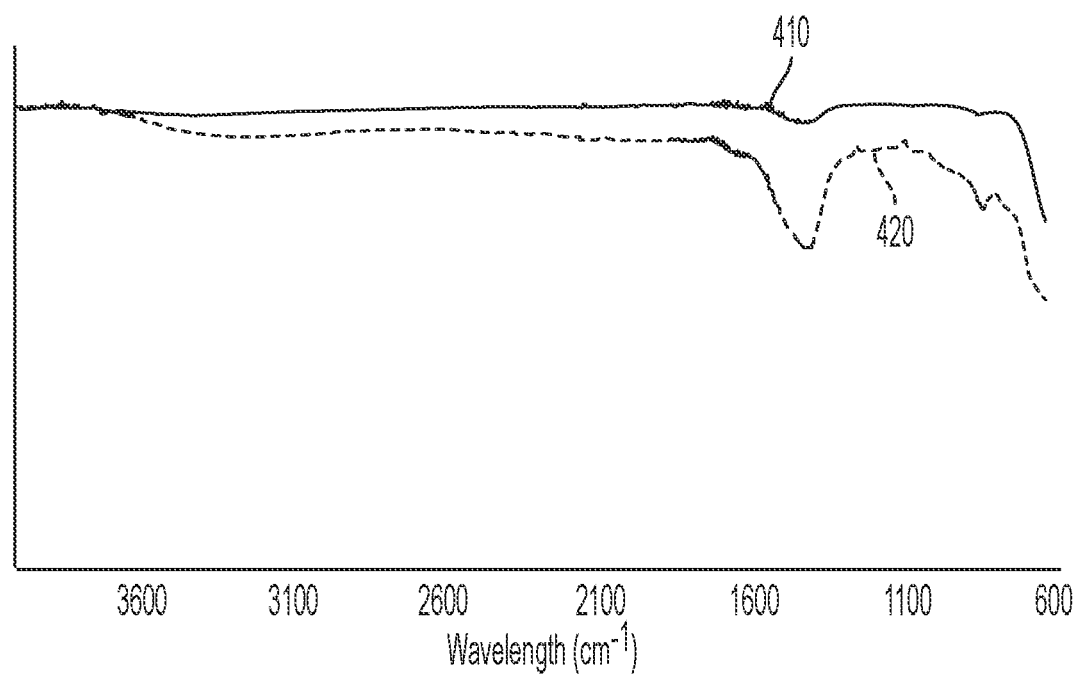
FIG. 4 graphically depicts the Fourier-transform infrared spectroscopy (FTIR) spectra of isomerization catalysts, according to one or more embodiments of the present disclosure.

The structures of the catalysts of Examples 1 and 2 were also analyzed with measured Fourier-transform infrared spectroscopy (FTIR) spectra. The FTIR spectra of the catalyst of Comparative Example 1 (410) and the catalyst of Inventive Example 2 (420) are depicted in FIG. 4. The spectra show the appearance of an OH stretching band (2900-3600 $cm_{-i}$) and an OH bending band (1300-1600 $cm_{-i}$) that correspond to incorporation of acidic sites to the surface of Inventive Example 2. Further, it is noted that small amounts of acid are shown as remaining in the Inventive Example 2 sample as indicated by the presence of a small S=O band (1134 $cm_{-i}$). The additional addition of the acidic sites to the surface of Inventive Example 2 are believed to be at least partially responsible for the increased 1-butene production and selectivity demonstrated by Inventive Example 2 when matched to the Comparative Examples.

Evaluation of Catalyst Properties

The mechanical properties of the catalyst of Inventive Example 2, as well as the catalysts of Comparative Examples 1 and 4, were determined and provided in Table 1. In particular, the surface areas of the catalysts were determined by the Brunauer Emmett-Teller (BET) method, the cumulative volume of pores and the average pore width were determined by the Barrett, Joyner, and Halenda (BJH) method, and the average particle sizes were calculated by the Scherrer equation. The properties of the catalysts of Inventive Example 2 and Comparative Examples 1 and 4 are provided in Table 1.

TABLE 1

| Catalyst Properties | | | | |
|---|---|---|---|---|
| Catalyst | Surface Area ($m^2/g$) | Cumulative Volume of Pores ($cm^3/g$) | Average Pore Width (Å) | Average Particle Size (Å) |
| Comparative Example 1 (Hydrothermal MgO, pH 11) | 177.79 | 0.27 | 57.27 | 337.48 |
| Inventive Example 2 (Hydrothermal MgO, pH 11, $H_2SO_4$ soak) | 46.21 | 0.16 | 80 | 235 |
| Comparative Example 4 (Commercially-Available Magnesium Oxide) | 60.49 | 0.30 | 184.41 | 991.91 |

As shown by Table 1, the catalyst of Inventive Example 2 had a significantly reduced surface area and pore volume compared to the catalysts of Comparative Examples 1 and 4. As shown by the results of the subsequently presented Catalytic Performance Evaluations, the catalyst of Inventive Example 2 also resulted in greater 1-butene yields than each of Comparative Examples 1, 3, and 4. This may suggest that the acid leaching with the sulfuric acid solution in accordance with Inventive Example 2 may directly contribute to improved isomerization catalytic activity.

Evaluation of Catalyst Performances at 400° C.

The catalysts of Inventive Example 2 and Comparative Examples 1 and 3, were tested for activity and selectivity for isomerizing a butene-containing feed to 1-butene in a fixed-bed continuous flow reactor, such as the reactor depicted in FIG. 2, at atmospheric pressure. A fixed amount of 0.1 g of each catalyst was pressed and sieved to a desired particle size in the range of 212-300 microns (μm), and was packed into a reactor tube. Layers of silicon carbide were positioned both upstream and downstream of the catalysts in order to ensure that the catalysts remained within the desired isothermal range.

Each reactor was first heated to 120° C. under nitrogen at a flow rate of 120 milliliters per minute (mL/min) and argon at a flow rate of 6 mL/min for 24 hours in order to ensure slow moisture desorption from the catalysts and identify any potential gas leaks from the reactors. The catalysts were then activated under nitrogen at 550° C. and a flow rate of 120 mL/min for 24 hours. The reactors were then cooled to 400° C. under nitrogen before a feedstock of cis-2-butene was passed through the reactors at a flow rate of 0.004 grams per minute (g/min) and a weight hourly space velocity (WHSV)

of 2.4 per hour (h$^{-1}$) for 48 hours. Quantitative analysis of the products for each reactor was performed using a gas chromatograph (commercially available as Agilent GC-7890B) with a thermal conductivity detector (TCD) and two flame ionization detectors (FID).

Figure 5:
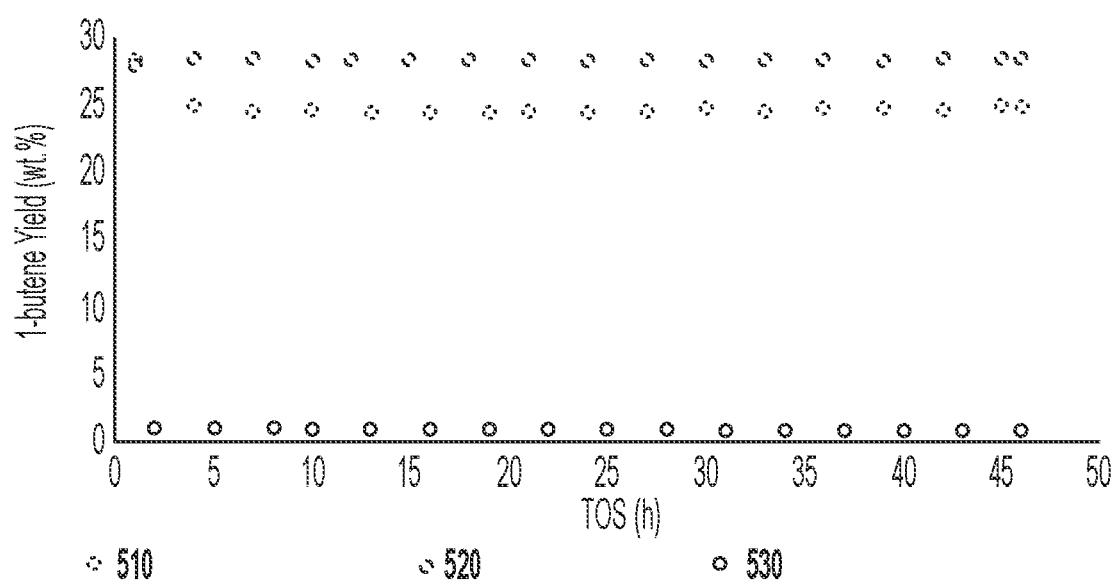
FIG. 5 graphically depicts the 1-butene yield (y-axis) as a function of time-on-stream (x-axis) obtained from a reactor for isomerizing a butene-containing feedstock, according to one or more embodiments of the present disclosure.

The 1-butene yield (wt. %) as a function of time-on-stream (TOS) for reactors comprising the catalyst of Comparative Example 1 (510), the catalyst of Inventive Example 2 (520), and the catalyst of Comparative Example 3 (530) are depicted in FIG. 5. As shown by FIG. 5, there was a demonstrated increase in the isomerization catalytic activity in the catalyst of Inventive Example 2 (MgO treated with $H_2SO_4$) compared to Comparative Example 1 (untreated MgO). Specifically, Inventive Example 2 maintained a 1-butene yield in excess of 28 wt. % compared to the 1-butene yield of less than 25 wt. % for Comparative Example 1. This represents an increase in 1-butene yield in excess of 14% and an increase in 1-butene selectivity in excess of 23% as a result of the sulfuric acid treatment of Inventive Example 2. The precise 1-butene yield and selectivity values are provided in Table 2.

A review of the catalytic performance illustrated in FIG. 5 also demonstrates that the improved performance of $H_2O_4$ treatment (Inventive Example 2) is not extended to treatment with a HCl acid solution (Comparative Example 3). Specifically, while Inventive Example 2 ($H_2SO_4$ treatment) maintained a 1-butene yield in excess of 28 wt. %, Comparative Example 3 (HCl treatment) was virtually inactive toward 2-butene isomerization with a 1-butene yield of less than 0.8 wt. %. Such performance of the HCl treated MgO (Comparative Example 3) indicates that not every acid is capable of yielding similar improved catalytic performance as described with the $H_2SO_4$ treatment in Inventive Example 2.

Evaluation of Catalyst Performances at 500° C.

The catalysts of Inventive Example 2 and Comparative Examples 1 and 3, were tested again, according to the same process as previously described in Evaluation of Catalyst Performances at 400° C., but at a reactor temperature of 500° C. for 48 hours.

Similar to the performance at 400° C., there was also a demonstrated increase in the isomerization catalytic activity in the catalyst of Inventive Example 2 (MgO treated with $H_2SO_4$) compared to Comparative Example 1 (untreated MgO) at 500° C. Specifically, Inventive Example 2 maintained a 1-butene yield of 27.8 wt. % compared to the 1-butene yield of 26.8 wt. % for Comparative Example 1. This represents an increase in 1-butene yield of 3.7% and an increase in 1-butene selectivity in excess of 8% as a result of the sulfuric acid treatment of Inventive Example 2. The complete 1-butene yield and selectivity values are provided in Table 2.

TABLE 2

Catalyst Performance

| Temperature (° C.) | Material | 1-butene Yield (wt. %) | 1-butene Selectivity | % improvement (1-butene Yield) |
|---|---|---|---|---|
| 400 | MgO | 24.841 | 0.416 | 14.1% |
|  | MgO treated with $H_2SO_4$ | 28.356 | 0.515 |  |
| 500 | MgO | 26.800 | 0.384 | 3.7% |
|  | MgO treated with $H_2SO_4$ | 27.784 | 0.415 |  |

It will be apparent to those skilled in the art that various modifications and variations can be made without departing from the spirit or scope of the disclosure. Since modifications, combinations, sub-combinations and variations of the disclosed embodiments incorporating the spirit and substance of the disclosure may occur to persons skilled in the art, the scope of the disclosure should be construed to include everything within the scope of the appended claims and their equivalents.

In a first aspect of the present disclosure, a method of producing an isomerization catalyst comprises preparing a catalyst precursor solution comprising at least a magnesium precursor, a hydrolyzing agent, and cetrimonium bromide; hydrothermally treating the catalyst precursor solution to produce a magnesium oxide precipitant; calcining the magnesium oxide precipitant to produce an isomerization catalyst precursor; soaking the isomerization catalyst precursor in an acid solution comprising sulfuric acid to produce an isomerization catalyst precursor precipitant; and calcining the isomerization catalyst precursor precipitant to produce the isomerization catalyst.

A second aspect of the present disclosure may comprise the method of the first aspect where the molar ratio of the magnesium precursor to the hydrolyzing agent in the catalyst precursor solution is from 1:10 to 1:1.

A third aspect of the present disclosure may comprise the method of the first or second aspects where the molar ratio of the magnesium precursor to cetrimonium bromide in the catalyst precursor solution is from 1:0.01 to 1:0.1.

A fourth aspect of the present disclosure may comprise the method of any of the first through third aspects where the method further comprises adjusting the pH of the catalyst precursor solution.

A fifth aspect of the present disclosure may comprise the method of the fourth aspect where the pH of the catalyst precursor solution is adjusted to a pH of from 8 to 12.

A sixth aspect of the present disclosure may comprise the method of the fourth aspect where the pH of the catalyst precursor solution is adjusted to a pH of from 9 to 11.

A seventh aspect of the present disclosure may comprise the method of any of the first through sixth aspects where hydrothermally treating the catalyst precursor solution comprises heating the catalyst precursor solution to a temperature of from 100° C. to 140° C. for a duration of from 48 hours to 96 hours.

An eighth aspect of the present disclosure may comprise the method of any of the first through seventh aspects where calcining the catalyst precipitant comprises heating the catalyst precipitant to a temperature of from 450° C. to 650° C. for a duration of from 1 hour to 10 hours.

A ninth aspect of the present disclosure may comprise the method of any of the first through eighth aspects where calcining the catalyst precipitant comprises heating the catalyst precipitant to a temperature of from 450° C. to 650° C. for a duration of from 1 hour to 10 hours.

A tenth aspect of the present disclosure may comprise the method of any of the first through ninth aspects where the acid solution is a 0.5M to 1.2M sulfuric acid solution.

An eleventh aspect of the present disclosure may comprise the method of any of the first through tenth aspects where the isomerization catalyst precursor is soaked in the acid solution for 5 to 30 minutes.

A twelfth aspect of the present disclosure may comprise the method of any of the first through tenth aspects where the isomerization catalyst precursor is soaked in the acid solution for 10 to 20 minutes.

A thirteenth aspect of the present disclosure may comprise an isomerization catalyst made by the method of any of the first through twelfth aspects.

A fourteenth aspect of the present disclosure may comprise the catalyst of the thirteenth aspect where the BET surface area of the isomerization catalyst is less than 100 $m^2/g$.

A fifteenth aspect of the present disclosure may comprise the catalyst of the thirteenth aspect where the BET surface area of the isomerization catalyst is from 25 $m^2/g$ to 60 $m^2/g$.

In a sixteenth aspect of the present disclosure, a method of producing 1-butene from a 2-butene-containing feedstock may comprise contacting the 2-butene-containing feedstock with an isomerization catalyst to produce an isomerization reaction effluent comprising 1-butene, the isomerization catalyst prepared by the method of any of the first through twelfth aspects.

A seventeenth aspect of the present disclosure may comprise the method of the sixteenth aspect where the isomerization catalyst is disposed in an isomerization reaction zone.

An eighteenth aspect of the present disclosure may comprise the method of the sixteenth or seventeenth aspects where contacting the 2-butene-containing feedstock with the isomerization catalyst causes the isomerization of at least a portion of 2-butene in the 2-butene-containing feedstock.

It should now be understood that various aspects of the present disclosure are described and such aspects may be utilized in conjunction with various other aspects.

It is noted that one or more of the following claims utilize the term "where" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated or included quantitative values of a given property are contemplated in this disclosure. It should be appreciated that compositional ranges of a chemical constituent in a stream or in a reactor should be appreciated as containing, in some embodiments, a mixture of isomers of that constituent. For example, a compositional range specifying butene may include a mixture of various isomers of butene. It should be appreciated that the examples supply compositional ranges for various streams, and that the total amount of isomers of a particular chemical composition can constitute a range.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the appended claims should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A method of producing an isomerization catalyst, the method comprising:
   preparing a catalyst precursor solution comprising at least a magnesium precursor, a hydrolyzing agent, and cetrimonium bromide;
   adjusting the pH of the catalyst precursor solution;
   hydrothermally treating the catalyst precursor solution to produce a magnesium oxide precipitant;
   calcining the magnesium oxide precipitant to produce an isomerization catalyst precursor;
   soaking the isomerization catalyst precursor in an acid solution comprising sulfuric acid to produce a isomerization catalyst precursor precipitant; and
   calcining the isomerization catalyst precursor precipitant to produce the isomerization catalyst.

2. The method of claim 1, where the molar ratio of the magnesium precursor to the hydrolyzing agent in the catalyst precursor solution is from 1:10 to 1:1.

3. The method of claim 1, where the molar ratio of the magnesium precursor to cetrimonium bromide in the catalyst precursor solution is from 1:0.01 to 1:0.1.

4. The method of claim 1, where the pH of the catalyst precursor solution is adjusted to a pH of from 8 to 12.

5. The method of claim 1, where hydrothermally treating the catalyst precursor solution comprises heating the catalyst precursor solution to a temperature of from 100° C. to 140° C. for a duration of from 48 hours to 96 hours.

6. The method of claim 1, where the acid solution is a 0.5M to 1.2M sulfuric acid solution.

7. The method of claim 1, where the isomerization catalyst precursor is soaked in the acid solution for 10 to 20 minutes.

8. An isomerization catalyst produced by the method of claim 1.

9. The isomerization catalyst of claim 8, where the BET surface area of the isomerization catalyst is less than 100 $m^2/g$.

10. The isomerization catalyst of claim 8, where the BET surface area of the isomerization catalyst is from 25 $m^2/g$ to 60 $m^2/g$.

11. A method of producing 1-butene from a 2-butene-containing feedstock, the method comprising:
   contacting the 2-butene-containing feedstock with an isomerization catalyst to produce an isomerization reaction effluent comprising 1-butene, the isomerization catalyst prepared by a method comprising:
   preparing a catalyst precursor solution comprising at least a magnesium precursor, a hydrolyzing agent, and cetrimonium bromide;
   hydrothermally treating the catalyst precursor solution to produce a magnesium oxide precipitant;
   calcining the magnesium oxide precipitant to produce an isomerization catalyst precursor;
   soaking the isomerization catalyst precursor in an acid solution comprising sulfuric acid to produce a isomerization catalyst precursor precipitant; and
   calcining the isomerization catalyst precursor precipitant to produce the isomerization catalyst.

12. The method of claim 11, where contacting the 2-butene-containing feedstock with the isomerization catalyst causes the isomerization of at least a portion of 2-butene in the 2-butene-containing feedstock.

13. The method of claim 11, where the molar ratio of the magnesium precursor to the hydrolyzing agent in the catalyst precursor solution is from 1:10 to 1:1.

14. The method of claim 11, where the molar ratio of the magnesium precursor to cetrimonium bromide in the catalyst precursor solution is from 1:0.01 to 1:0.1.

15. The method of claim 11, further comprising adjusting the pH of the catalyst precursor solution.

16. The method of claim 15, where the pH of the catalyst precursor solution is adjusted to a pH of from 8 to 12.

17. The method of claim 11, where the BET surface area of the isomerization catalyst is less than 100 $m^2/g$.

18. The method of claim 11, where the acid solution is a 0.5M to 1.2M sulfuric acid solution.

19. The method of claim 11, where the isomerization catalyst precursor is soaked in the acid solution for 10 to 20 minutes.

* * * * *